(12) United States Patent
Bjerregaard

(10) Patent No.: US 8,579,850 B2
(45) Date of Patent: Nov. 12, 2013

(54) IRRIGATION DEVICE AND METHOD OF USING THE DEVICE

(75) Inventor: Henrik Bork Bjerregaard, Bronshoj (DK)

(73) Assignee: MBH-International A/S, Allerød (DK)

( * ) Notice: Subject to any disclaimer, the term of this patent is extended or adjusted under 35 U.S.C. 154(b) by 10 days.

(21) Appl. No.: 13/389,518

(22) PCT Filed: Aug. 25, 2010

(86) PCT No.: PCT/DK2010/050219
§ 371 (c)(1),
(2), (4) Date: Feb. 8, 2012

(87) PCT Pub. No.: WO2011/023196
PCT Pub. Date: Mar. 3, 2011

(65) Prior Publication Data
US 2012/0143168 A1    Jun. 7, 2012

(30) Foreign Application Priority Data
Aug. 26, 2009  (DK) .............................. 2009 00963

(51) Int. Cl.
*A61M 1/00*    (2006.01)
(52) U.S. Cl.
USPC ............................. 604/27; 604/514; 604/132
(58) Field of Classification Search
USPC .......................... 604/514, 132, 19, 27, 36, 37
See application file for complete search history.

(56) References Cited

U.S. PATENT DOCUMENTS

| 3,065,750 A | 11/1962 | Mandell | 128/229 |
| 5,074,842 A | 12/1991 | Clayton | 604/54 |
| 2006/0129135 A1* | 6/2006 | Moeller-Jensen et al. | 604/540 |

FOREIGN PATENT DOCUMENTS

| DK | DE 585360 | 4/1931 |
| EP | 1 531 885 B1 | 5/2005 |
| GB | 7078 | 0/1911 |
| WO | WO 98/23312 | 6/1998 |
| WO | WO 2004/006993 A1 | 1/2004 |
| WO | WO 2009/080050 A1 | 7/2009 |

OTHER PUBLICATIONS

International Search Report and Written Opinion, PCT/DK2010/050219, mailed Nov. 15, 2010.

* cited by examiner

*Primary Examiner* — Kevin C Sirmons
*Assistant Examiner* — Deanna K Hall
(74) *Attorney, Agent, or Firm* — Winston & Strawn LLP

(57) ABSTRACT

An irrigation device that includes a reservoir for an irrigating liquid, a catheter in liquid communication with the reservoir, a fixation member for fixation of the catheter and a control unit. The control unit is arranged for in a first position transferring the irrigation liquid to the fixation member and in a second position transferring the irrigation liquid to the catheter. Thereby is provided a simple, inexpensive and essentially maintenance free device which can be used for administrating an irrigation liquid, and which at the same time comprises a fixation member that will not be expelled from the body cavity by e.g. a peristaltic reflex, during use.

17 Claims, 3 Drawing Sheets

IRRIGATION DEVICE AND METHOD OF USING THE DEVICE

This application is a 371 filing of International Patent Application PCT/DK2010/050219 filed Aug. 25, 2010.

BACKGROUND

The present invention relates to an irrigation device comprising a reservoir for an irrigating liquid, a catheter in fluid communication with the reservoir, a fixation member, and a control unit arranged for in a first position transferring the irrigation liquid to the fixation member and in a second position transferring the irrigation liquid to the catheter.

Administrating an irrigation liquid is a common medical procedure whereby liquid is injected into the rectum and lower intestine of a patient in order to induce bowel movement. The need for such a procedure typically arises in patients suffering from certain physical ailments in which voluntary bowel control is impaired or when the bowel needs to be cleaned before e.g. a coloscopy or a surgical operation.

Medical equipment currently exists in the art for administering an irrigation liquid to patients in need of this procedure, e.g. from international patent publication no. WO 98/23312, where the irrigation medium is fed by gravity from a bag hung from a frame arranged close to the patient. As the operation is dependent on gravity, the system cannot be readily portable, which is often very important if the patient should lead a normal life.

Although some conventional systems are mobile, they are heavy and cumbersome, and are thus not readily transportable by the user. Consequently, they tend to be restricted to use in hospitals or nursing homes.

However, irrigation liquids often needs to be administered to a patient at home when the need for medical assistance does not necessitate a doctor or another health care assistant. In this respect it is often difficult for the patient to administer the irrigation liquid to himself or herself since the conventional irrigation devices often causes discomfort and irritation when being inserted. Moreover, it is difficult for the patient to administer the liquid while steadily holding the irrigation liquid in the required area. Often another individual assists the patient but assistance may not always be available, if for instance, the patient lives alone. Thus there is also a need for an irrigation device that effectively can be used for self-administration of irrigation liquids.

The self-administration of irrigation liquids using the conventional irrigation systems may furthermore be especially difficult for elderly or patients having physical problems, not only due to the complexity of the systems but also since the systems require the use of many different components to work together. The catheter needs to be inserted, the pump must be activated and the correct dose of liquid must be delivered.

Although it at first sight would be advantageous simply to make a very simple device without e.g. a pump and/or other control units, such modifications may adversely affect other desirable features of the device. In particular, it is desirable to prevent any reflux of liquid back into the reservoir after the irrigation liquid has been delivered, and it is desirable to ensure that the catheter is correctly keep in place during the addition of irrigation fluid to the body cavity. A simplification of the device may compromise these features.

In order to meet some of the drawbacks with the known irrigation systems, U.S. Pat. No. 5,074,842 describes an irrigation system, which comprises a tube and a balloon for retaining the tube in the rectum. Said balloon can be inflated after the insertion of the tube. The balloon is inflated using air, which is delivered through a syringe valve which communicates with an air passage. A similar system is known from European patent publication no. 1531885, which describes an irrigation system comprising a reservoir, and an air inflated balloon for fixation of a tube in the rectum.

Even thought the balloon in these known systems will assist the patient by helping to keep the catheter in the correct place during the irrigation, the systems have the major drawback that the balloon cannot safely keep the tube in place during use due to the fact that the air filled balloon reacts to the body movements, e.g. peristaltic reflexes, resulting in that the catheter inconveniently may fall out of the body cavity. This is not only unwelcoming for the patient but also very demeaning, as the surroundings inevitability will be contaminated with irrigation liquid and bodily fluids.

Furthermore, since air is used to inflate the balloon in these known systems, additional elements are needed in the systems in order to ensure that the air can be delivered to the surroundings instead of into the body cavity. If the air was delivered at the body cavity this would result in an additional distending or dilation of said body cavity resulting in additional pain and discomfort for the patient.

International patent publication no. WO 2009/080050 relates to a probe for use in connection with anal irrigation. Said prove comprises a tip part, a shaft part and an expandable balloon for retaining the probe in the rectum. The balloon is connected to the probe in such a way that when irrigation liquid is added to the probe the balloon starts to expand. This expansion will continue until the maximum expansion is achieved at which point the tip part and shaft part will start to be dislodged in relation to each other providing a flow path between the reservoir and the tip part. In order for an irrigation to take place, the complete volume of irrigation liquid will have to pass through the expandable balloon. Said balloon will continually expand which can lead to great discomfort and pain for the user. Furthermore, as all irrigation liquid has to pass the balloon it is not possible to e.g. minimize the expansion of the balloon during use.

From British patent publication no. 191107078 is also known an irrigation device comprising a probe and a retaining member, which can expand using irrigation liquid. However when the extended retaining member is to be emptied, this will have to be performed by disconnecting the device to the supply of irrigation liquid and allowing a backflow of liquid from the expanded retaining member either unrestricted into the surroundings, leading to contamination of the surroundings, or alternatively back into the reservoir of irrigation liquid, leading to contamination of the reservoir. Furthermore, the device in GB191107078 comprises no means for preventing backflow from the site of irrigation during use.

SUMMARY OF THE INVENTION

Therefore, it is a first aspect of the present invention to provide an irrigation device that safely and effectively can administer an irrigation liquid to a patient without causing discomfort.

It is a second aspect of the present invention to provide an irrigation device where an expandable retaining member can be individually adjusted during the irrigation process.

It is a third aspect of the present invention to provide an irrigation device where the liquid is easier to administer, and that keeps the catheter safely in place during the administration of the irrigation liquid.

It is a forth aspect of the present invention to provide an irrigation device that prevents reflux of liquid into the container after use and/or prevents leakage of the liquid prior to use.

In a fifth aspect according to the present invention is provided an irrigation device of the kind mentioned in the opening paragraph that is inexpensive to manufacture and is simple and reliable to use.

In a sixth aspect according to the present invention is provided an irrigation device of the kind mentioned in the opening paragraph that are relatively easy to operate, especially by the patient and therefore can be used for self-administration.

These and further aspects are achieved according to the present invention as the control unit further is arranged for in a third position providing a fluid path between the fixation member and the catheter for discharging irrigation liquid from the fixation member through the catheter i.e. the irrigation liquid transferred to the fixation member in the first position is allowed to flow out of the fixation member and be discharged through the catheter.

The fluid path between the fixation member and the catheter in the third position of the control unit will ensure when the fixation member is deflated, e.g. during efflux or withdrawal of the irrigation liquid from the fixation member, said liquid will be transferred and emptied in the body cavity though an opening in the catheter, whereby the device according to the invention ensures that it is possible to irrigate a body cavity without the patient and the surroundings getting wet and which at the same time meets the demand for solving the problem of deflating the fixation member.

In an especially simple embodiment the irrigation liquid from the fixation member is discharged via the same opening used for administrating the irrigation liquid to the body cavity.

Furthermore, since the irrigation liquid is used for both expanding the fixation member and irrigating the body cavity, a very simple and inexpensive system with only a very few components is provided.

When the irrigation device according to the present invention is used for anal irrigation, the intestinal wall may be subjected to peristaltic movement and then the intestinal wall may move outwards or inwards. However as the control unit will be placed in a first position when the fixation member is expanded and in a second position when the irrigation liquid via the catheter is added to the body cavity, a user has the possibility of independently and individually adjust the expansion of the fixation member, e.g. based on the peristaltic movement but also based on an individually needs and desires.

Thus, independently of the site of irrigation, if the expansion of the fixation member e.g. is found to be so large such that the fixation member e.g. causes discomfort, the user can conveniently switch the control unit to the third position and withdraw a part of the liquid in the fixation member. Said irrigation liquid will in the third position simply be dislocated from the fixation member to the rectum via the catheter, and no further measures therefore have to be taken. In a similar manner, if the expansion of the fixation member is insufficient, the user can easily switch the control unit to the first position whereby the fixation member is further expanded. Thus the user can throughout the irrigation process adjust the degree of expansion of the fixation member simply by using the control unit. Furthermore, as the irrigation liquid in all situations will be passed directly to the site of irrigation, the surroundings will never be contaminated with irrigation liquid and/or bodily fluids.

The use of an incompressible fluid, i.e. the irrigation liquid, for expanding the fixation member, ensures that the fixation member becomes more rigid than hitherto known thereby ensuring that the fixation member and the catheter will not be expelled from the body cavity by e.g. a peristaltic reflex during use. Thus, by using the irrigation device according to the invention a better and safer fixation of the irrigation device is obtained than with the conventional systems.

Expanding of the fixating member and the flow of irrigating liquid are controlled by the control unit, which may be e.g. held by the user or positioned at a place near said user. The catheter can easily be inserted in the relevant body cavity e.g. the rectum, before the fixation member is expanded.

The following expansion of the fixation member and the flow of irrigating liquid to the catheter are controlled by the user in a simple manner by setting the control unit into the appropriate sequential positions. Advantageously, the control unit provides the user with a logical indication of the operational steps to be carried out in order to perform the irrigation.

The simplicity of the irrigation device according to the invention ensures that any patient or user, e.g. an elderly person without undue efforts can use the device for self-administrating an irrigation liquid. Since the irrigation liquid in all circumstances, both during irrigating and when the fixation member is emptied, will be discharged through the catheter, and thereby into the patients rectum it is ensured that all irrigation liquid inevitable will be displaced to/in e.g. a toilet or bedpan. Using the device according to the invention will therefore significantly reduce the discomfort and inconvenience of the patient associated with the known systems.

In order to prevent an undesired backflow of irrigation liquid from the site of irrigation, e.g. liquid and faeces during anal irrigation, into the device, e.g. the reservoir, the device according to the invention can preferably comprise means for preventing a back flow of liquid thereby precluding any contamination of the reservoir, and it's remaining content, which may occur after administration of the liquid to a patient. Said means will preferably also ensure that other parts of the device are not contaminated.

Furthermore, since backflow efficiently is prevented the device according to the invention can easily be used for several applications, e.g. by refilling the reservoir with irrigation liquid. Furthermore, the administration of the irrigation liquid can take as long as the patient need or require without compromising the function of the device according to the invention.

Said means can advantageously be one or more one-way valves. It is preferred that the one-way valve is placed in connection with the catheter, e.g. close to the tip of the catheter. However said at least one one-way valve can also be placed e.g. after the control unit.

The one-way valves is preferably chosen from the group consisting of slit valves, check valves including swing valves, lift valves, ball valves, tilting disk valves, dual plate (leaflet) valves, diaphragm valves, flap valves and general valves including ball valves, butterfly valves, check valves, diaphragm valves, gate valves, globe valves, plug valves, duck bill valves and pinch valves. The one-way valves can be with or without preload, and be either identical or different from each other. The only demand is that the valves are capable of provide the desired properties to the device according to the invention, i.e. ensuring that the flow of fluid is uni-directional.

In an advantageous embodiment, the control unit comprises at least two elements that may be moved with respect to each other into at least the first position transferring the irrigation liquid to the fixation member, the second position transferring the irrigation liquid to the catheter and the third position for discharge the irrigation liquid transferred to the fixation member in the first position via the catheter.

Such a design will not only ensure that the control unit is simple, compact and functional but also that the unit is almost maintenance free and inexpensive.

In this respect the dimensions of the device is preferably such that the user can control all parts of the device without undue effort, i.e. the control unit is spaced from the catheter and the fixation member such that the control unit conveniently can be operated.

When the control unit is set in the first position the fluid path between the reservoir and the fixation member is established, ensuring that irrigation liquid expands the fixation member by filling its lumen. The fluid path to the catheter is preferably not open. When the control unit is set in the second position, the path to the fixation member is preferably closed simultaneously opening a liquid path to the catheter from the reservoir, ensuring that irrigation liquid can be transferred from the reservoir to the catheter without influencing the fixation member.

When the control unit is set in the third position only a fluid path between the fixation member and the catheter is provided, whereby liquid present in the expanded fixation member will be allowed to flow out via/through the catheter. This ensures that the user do not has to take any specific precautions when the catheter has to be removed from the site of irrigation, and the liquid from the fixation member will simply flow into the site of irrigation, efficiently preventing any contamination of the surroundings. Furthermore, as liquid was used to expand the fixation member the additional fluid from the fixation member will not cause any discomfort to the patient. All the user has to do is to switch the control unit to the third position, whereby the liquid in the fixation member automatically will be allowed to flow out of the catheter and into the site of irrigation.

In order to ensure that the device can dry between the different uses the control unit can also be set in an inactive position, i.e. a position that provides an open fluid path between all parts of the irrigation device according to the invention.

Thereby is ensured that all of the operational steps necessary in order to carry out irrigation, i.e. expansion of the fixation member, flow of irrigating liquid and deflation of the fixation member are controlled by an appropriate sequential adjustment of the control unit.

In order to ensure that the system according to the invention can be placed in any position with respect to the user and not necessarily at a level substantially higher than the user, the system preferably comprises a pump.

As the irrigation liquid is also used for expanding the fixation member in addition to the irrigation of a body cavity, the system according to the invention has the advantage that the same pump can be used for both actions.

The pump can e.g. be part of the control unit or be a separate unit. However, in order to keep the system according to the invention as simple as possible it is preferably that the pump is handheld, e.g. in the form of a bulb pump or a bellow pump, which both can be squeezed by the user's hand. Furthermore, such pumps provide a pleasant and comforting fit in the hand and requires small forces to activate.

Such a hand held pump can preferably comprise two one-way valves wherein the first one-way valve is adapted for allowing a fluid to enter the pump and the second one-way valve is adapted for allowing said fluid to be expelled from the pump.

Thereby is provided a simple, inexpensive and essentially maintenance free device which can be used for administrating an irrigation liquid, which at the same time prevents reflux of irrigation liquid and/or bodily fluids back into the irrigation system.

If the user lacks strength or has poor dexterity in their hands it may in some cases be easier for them to operate an electric pump rather than squeezing a bulb or a bellow pump. If an electric pump is applied in the present system the user only has to push a button to start the pump.

The irrigation liquid reservoir is in fluid communication with the catheter and the fixation means via the control unit. Accordingly, conduit means are provided having a first part connecting the reservoir with the control unit and a second and third part connecting the control unit with the catheter and the fixation member, respectively.

Preferably, the catheter and fixation member are arranged such that the fixation member comprises a seal, which preferably sealingly surrounds the catheter. Said seal provides a means for retain the irrigation liquid within the fixation member's interior and to secure the catheter to the balloon.

The fixation member may be of any shape, contour, size and volume, however the fixation member preferably has sufficient compliance to generally conform to the shape, contours, walls and structures of the respective body cavity, e.g. the rectum thereby exerting a compressive force. Also, male and female anatomy and subject size (e.g., adult vs. child) may dictate the shapes, contours, size and volume of the fixation member.

The fixation member may have folds, ribs, channels, undulations and/or other formations or contours to increase the expandable surface area of the fixation member, to facilitate expansion to a desired shape, or to enhance fixation member compliance to accommodate specific features, structures, tissues or organs of the body cavity.

The fixation member can be made of an expandable material, such as natural rubber, synthetic rubber, silicone, latex, urethane (polyurethane), polyvinylchloride, polyethylene, nylon or any other expansible elastomer, polymer or other material and is preferably, formed of a biocompatible, sterilizable material that may be treated with antimicrobial agents.

It should be recognized by one in the art that the system may be used for irrigation performed to any body cavity such as the uterus, the bowel (the intestinal system) and the bladder. Accordingly, the catheter will be inserted in an appropriate body cavity, e.g. the rectum or a stoma, and fixated in said body cavity by means of the fixation member.

In an advantageously embodiment the system according to the invention comprises means for ensuring that the fixation member cannot be expanded to an excessive degree, thereby preventing that the fixation member will burst during use. Said means could e.g. be a pressure-sensitive valve, which will control the pressure inside the fixation, member or the means can be a pressure gauge having an indication of the maximum pressure in the fixation member.

The system is preferably a closed system, i.e. the system is closed when the reservoir is filled with the desired liquid. This will ensure that the system easily can be carried and may be placed in any position with respect to the user and not necessarily at a level substantially higher than the user.

The reservoir may comprise an inlet for allowing the reservoir to be filled with new irrigation liquid. Said inlet can preferably be closable, e.g. by a screw-lid in order to prevent the irrigation liquid from being spilled, ensuring that the system becomes a closed system.

In a preferred embodiment the reservoir is either partly or fully transparent, such that the user can visually determine whether a liquid is present in the reservoir. The reservoir may advantageously comprise means for indicating the volume of the liquid contained in the reservoir such as indications on a sidewall of the reservoir.

In a preferred embodiment, the control unit comprises a housing and a rotatable cylinder placed inside the housing. The cylinder is preferably placed in the housing in a sealed manner in order to prevent the irrigation liquid from escaping from the control unit. Suitable sealing means are well known to the person skilled in the art, however a preferred sealing can be obtained by providing a tight fit between the cylinder and the housing.

The housing is provided with a first conduit tube for connecting the reservoir with the control unit, a second conduit tube for connecting the control unit with the catheter and a third conduit tube for connecting the control unit with the fixation member.

The second and third tube can preferably be incorporated into a single tube which can either be split into two tubes at the connection points with the catheter and the fixation member or have two lumens.

The rotatable cylinder is provided with a first through-going hole and/or channel for in the first position of the control unit transferring irrigation liquid from the reservoir to the fixation members and a second through going hole and/or channel for in the second position of the control unit transferring liquid from the reservoir to the catheter.

The respective holes and/or channels are arranged in the cylinder as to match the location of the conduit tubes in the housing.

The catheter can have any shape so long as the catheter is able to perform the function of administrating the irrigation liquid to the patient's body cavity. Thus, the catheter could be relatively cylindrical, conical, prismatic, prolate spheroidal or pyramidal or consist of a simple tube. Further, the catheter in whatever form it takes, could have smooth sides, ridges or undulations.

The catheter comprises an outlet for discharging the irrigation liquid, said outlet is placed at a distal end in the catheter.

In a preferred embodiment the catheter has a mainly fructoconical shape whose outside diameter progressively decreases from it's proximal end to it's distal end as said shape automatically will ensure a tight fit with the body cavity.

Irrigation liquid means any liquid, which is capable of irrigation the body cavity of interest. In order to stimulate bowel movements suitable irrigation liquids includes water, hypertonic aqueous salt solutions, solutions or suspensions of cathartic agents, such as bisacodyl or phenolphthalein, and mineral oil.

BRIEF DESCRIPTION OF THE DRAWINGS

The invention will be explained in greater detail below, describing exemplary embodiments of the intestinal irrigation device with reference to the drawing, in which.

DETAILED DESCRIPTION OF THE INVENTION

The invention is described below with the assumption that the device according to the present invention is used for administrating an irrigation liquid to the rectum. This assumption is not to be construed as limiting, and other liquids e.g. medications or more thorough irrigation procedures can also be administered or performed using the device.

Figure 1:
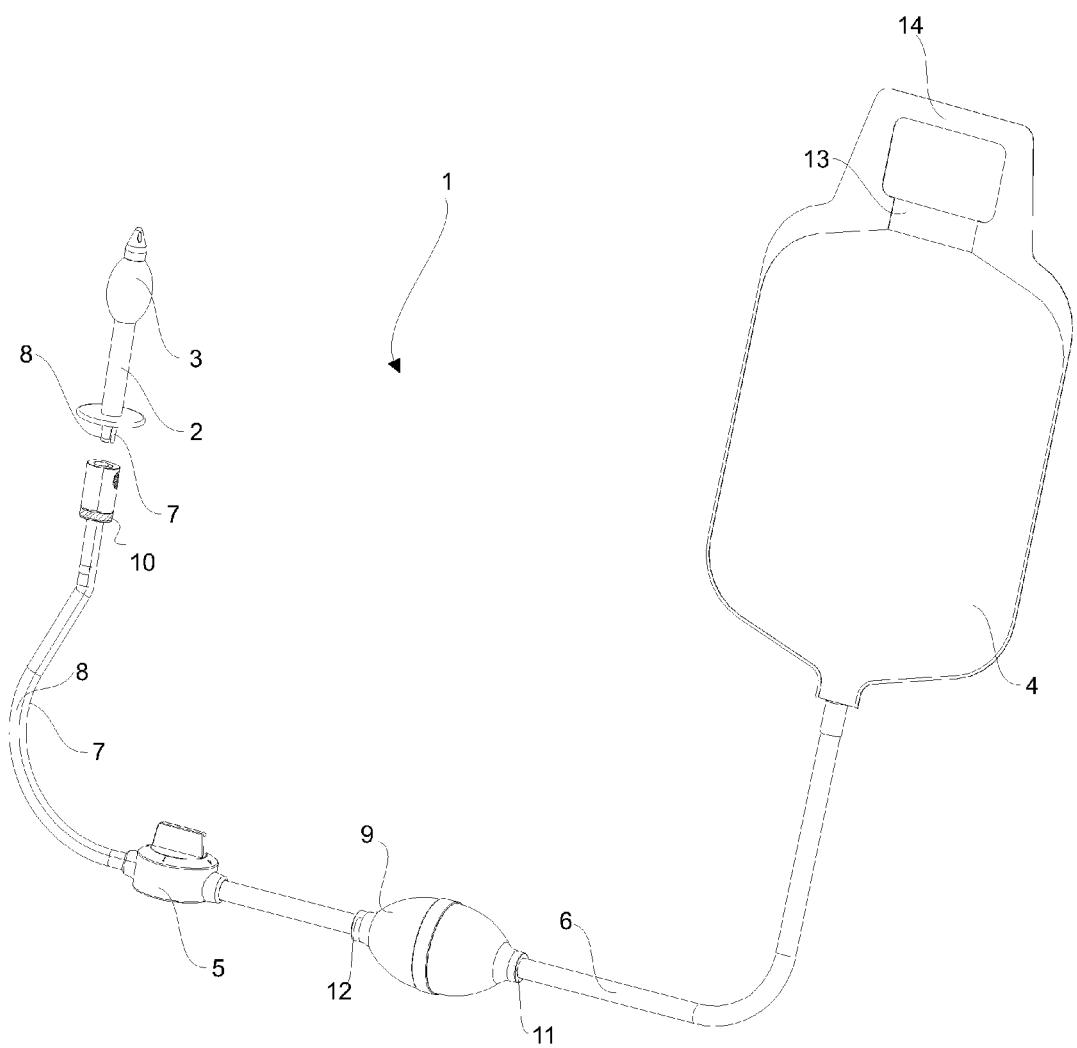
FIG. 1 shows a schematic view of an exemplary embodiment of a blank for the device according to the present invention.

In FIG. 1 the irrigation device 1 consist basically of a catheter 2 having an opening at the distal end for discharging irrigation liquid into the site of irrigation, an expandable fixation member 3, a reservoir 4 and a control unit 5.

A first conduit tube 6 connects the reservoir 4 with the control unit 5, a second conduit tube 7 connects the control unit 5 with the catheter 2 and a third conduit tube 8 connects the control unit 5 with the fixation member 3.

In the first conduit tube 6 is inserted a hand-held bellow pump which can be activated by squeezing by hand. Such pumps provide a pleasant and comforting fit in the hand and requires small forces to activate. A valve 10 for venting the conduit tubes during pumping action is also provided in communication with the second and third conduit tube 7,8. However it is understood that both the venting valve 10 and the pump 9 may be placed in any convenient location in the device.

In the embodiment shown two one-way valves 11, 12 are integrated with the pump. The first one-way valve 11 is adapted for allowing a liquid to enter the bellow pump 9 and the second one-way valve 12 is adapted for allowing said liquid to be expelled from the pump, when the pump is squeezed.

The reservoir 4 comprises an inlet 13 for allowing the reservoir to be filled and/or refilled with irrigation liquid. In the present embodiment the reservoir can via handle 14 be hanged on a handle or peg, but the reservoir could within the scope of the invention have any other convenient shape and/or form and could e.g. be a box having a bottom designed for simply standing on the floor.

The reservoir 4 can either be partly or fully transparent, such that the user can visually determine whether a liquid is present in the reservoir 4. The reservoir 4 may advantageously comprise means for indicating the volume of the liquid contained in the reservoir 4 such as indications on a sidewall of the reservoir 4.

The embodiment shown in FIG. 1 is inexpensive to manufacture as all parts of the device according to the invention is placed along a single string. This also makes the device 1 essentially maintenance free and since the device comprises a fixation member 3 that will not be expelled from the body cavity by e.g. a peristaltic reflex, during use the device 1 is not only simple but also reliable and convenient to use.

Figure 2:
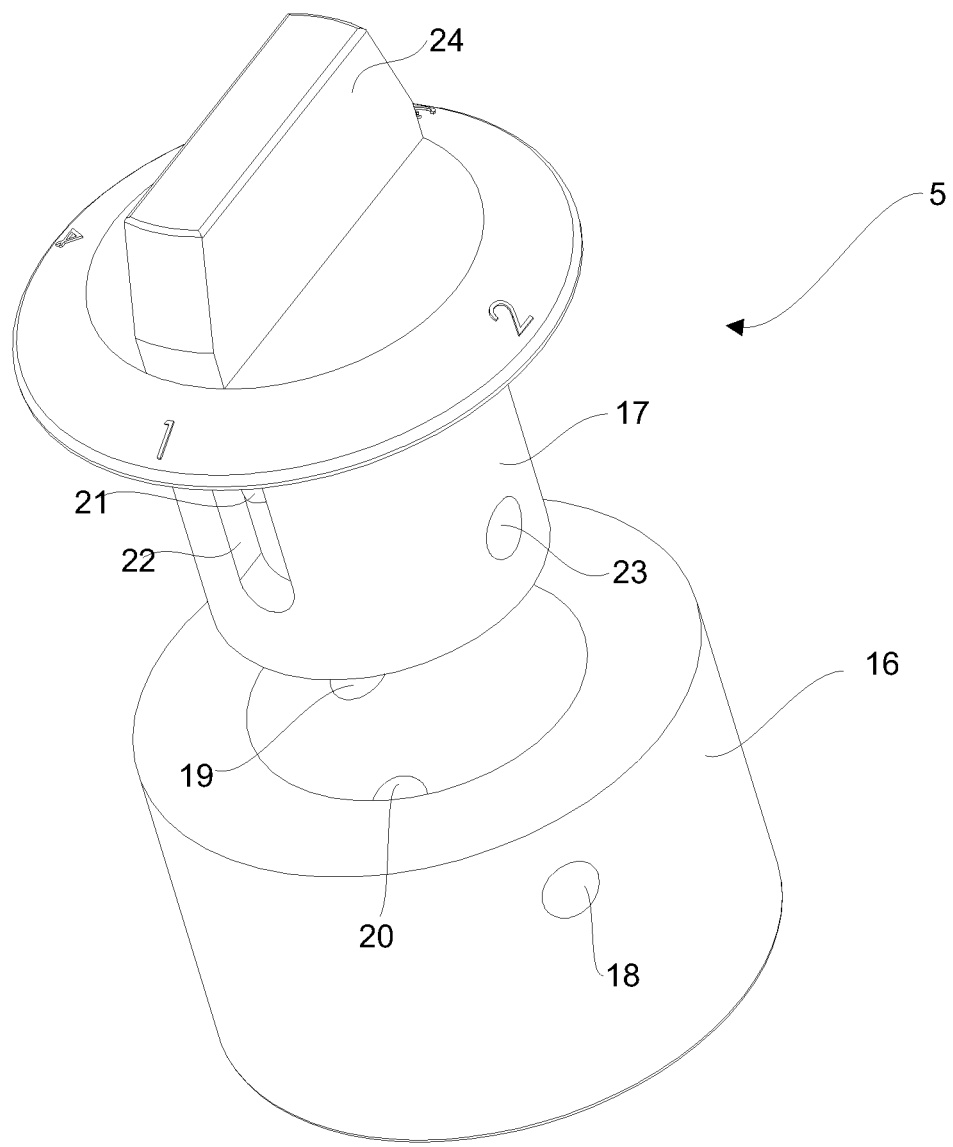
FIG. 2 shows a schematic view of a first embodiment of the control unit according to the present invention.

A first embodiment of the control unit 5 according to the present invention is shown in an exploded view in FIG. 2. The control unit 5 comprises a housing 16 and a rotatable cylinder 17 placed inside the housing 16, preferably in a sealed manner in order to prevent the irrigation liquid from escaping from the control unit 5.

The housing 16 is provided with three holes 18, 19, 20 for controlling the fluid communication between the reservoir 4, the catheter 2 and the fixation member 3.

The first hole 18 connects the first conduit tube 6 from the reservoir 4 to the control unit 5, the second hole 19 connects the control unit 5 with the catheter 2 via conduit tube 7 and the third hole 20, connects the control unit 5 with the fixation member 3 via the third conduit tube 8.

The second and third conduit tube 7, 8 can preferably be incorporated into a single tube which can either be split into two tubes at the connection points with the catheter 2 and the fixation member 3 or have two lumens.

The rotatable cylinder 17 is provided with a first through-going hole 21 placed in a recess 22, and a second through going hole 23, which optionally also can be placed in a similar recess.

The holes 21, 23 and the recess 22 are arranged in the cylinder 17 as to match the location of the holes 18, 19, 20 in the housing 16.

The cylinder 17 rotates in the housing 16 by means of turning knob 24. Said turning knob has in the embodiment shown the numbers 1-4 indicated on the surface, corresponding to the four operational positions of the control unit whereby the user visually is provided with the appropriate sequential positions of the cylinder 17 and a logical indication of the operational steps to be carried out in order to perform the irrigation.

The next operational position is easily reached simply by sequentially rotating the cylinder 90 degrees from one position to the next.

The flow of liquid in the control unit 5 is only schematically shown in FIG. 3.

Figures 3A, 3B:
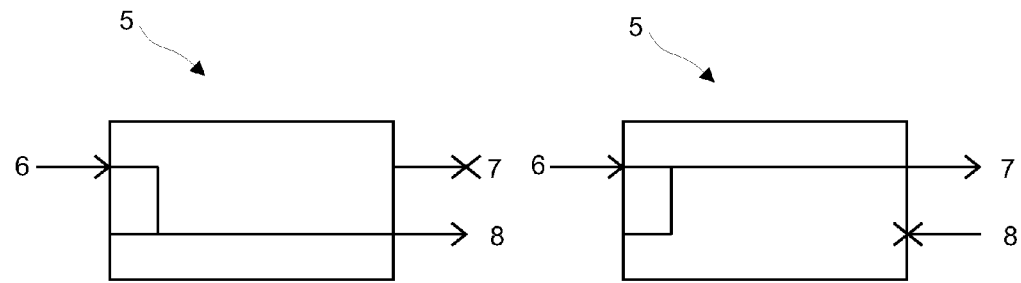
FIG. 3a shows a schematic view of the control unit according to the invention in a first stage of use for transferring irrigation liquid from the reservoir to the fixation member.
FIG. 3b shows a schematic view of the control unit according to the invention in a second stage of use for transferring irrigation liquid from the reservoir to the catheter.

In FIG. 3a the control unit 5 is set in the first position for transferring irrigation liquid from the reservoir 4 to the fixation member 3. The control unit 5 only allows the irrigation liquid to flow from the first conduit tube 6 to the third conduit tube 8, whereby action from the pump will ensure that the fixation member 3 expand.

When the fixation member 3 is sufficiently expanded the rotatable cylinder 17 is rotated 90 degrees placing the control unit 5 in the second position for transferring irrigation liquid from the reservoir 4 to the catheter 2. The second position is shown in FIG. 3b, and it can be seen that the irrigation liquid is allowed to flow from the first conduit tube 6 to the second conduit tube 7, whereby pumping action will transfer the desired volume via the catheter 2 to the body cavity.

Figures 3C, 3D:
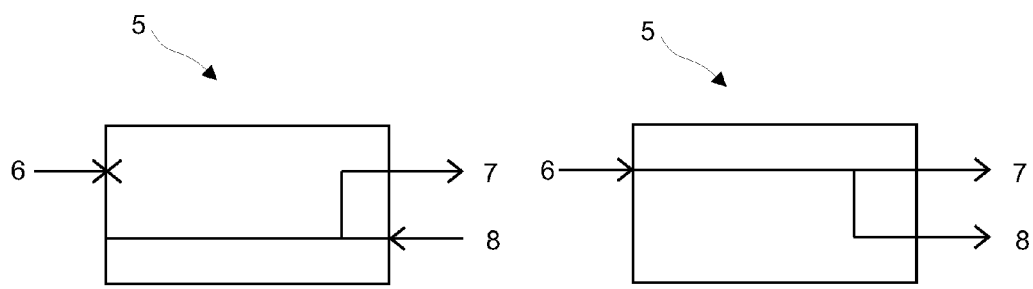
FIG. 3c shows a schematic view of the control unit according to the invention in a third stage of use for providing deflation of the fixation member, by efflux or withdrawal of the irrigation liquid from the fixation member.
FIG. 3d shows a schematic view of the control unit according to the invention in a forth stage of use, which allows flow between all parts of the irrigation.

After sufficient irrigation liquid has entered the body cavity the rotatable cylinder 17 is rotated another 90 degrees setting the control unit 5 in the third position in order to provide deflation of the fixation member 3, by efflux or withdrawal of the irrigation liquid from the fixation member 3, so that the catheter 2 may be removed from the body cavity of the subject. As can be seen in FIG. 3c the liquid from the fixation member is only allowed to flow into the catheter 2, thus the irrigation liquid from the fixation member 3 is emptied into the body cavity, whereby the device 1 according to the invention ensure that it is possible to irrigate a body cavity without the patient and the surroundings getting soiled and which at the same time meets the demand for solving the problem of deflating the fixation member 3.

When the fixation member 3 is deflated the catheter 2 can be removed from the rectum without causing any discomfort, and rotatable cylinder is then rotated another 90 degrees setting the control unit 5 in the inactive position seen in FIG. 3d, which allows flow between all parts of the irrigation device 1 whereby said parts can be dried and storage until the next use.

Modifications and combinations of the above principles and designs are foreseen within the scope of the present invention.

What is claimed is:

1. An irrigation device comprising a reservoir for an irrigating liquid, a catheter in liquid communication with the reservoir, a fixation member, and a control unit arranged for in a first position transferring the irrigation liquid to the fixation member and in a second position transferring the irrigation liquid to the catheter, wherein the control unit is arranged for in a third position providing a liquid path between the fixation member and the catheter for discharging irrigation liquid from the fixation member through the catheter.

2. The irrigation device according to claim 1, wherein the control unit is arranged for in an inactive position allowing at least the reservoir, the catheter and the fixation member of the irrigation device to be in fluid communication.

3. The irrigation device according to claim 1, further comprising means for preventing backflow into the reservoir or other parts of the device.

4. The irrigation device according to claim 3, wherein the means for preventing backflow is at least one one-way valve.

5. The irrigation device according to claim 1, wherein the control unit comprises at least two elements, which may be moved with respect to each other, into at least the first and second positions.

6. The irrigation device according to claim 5, wherein the positions of the control unit are sequentially arranged.

7. The irrigation device according to claim 1, further comprising at least one pump for pumping irrigation liquid from the reservoir to the fixation member or the catheter.

8. The irrigation device according to claim 1, wherein the catheter and fixation member are an integral unit wherein the fixation member, at least partly, sealingly surrounds the catheter.

9. The irrigation device according to claim 1, as a closed system.

10. A method of irrigating using the device according to claim 1, which comprises:
 placing the catheter into the site of irrigation,
 placing the control unit in the first position in order to transfer the irrigation liquid to the fixation member whereby the fixation member is expanded,
 placing the control unit in the second position in order to transfer the irrigation liquid to the catheter, and
 placing the control unit in the third position in order for discharging the irrigation liquid used to expand the fixation member.

11. The method according to claim 10, wherein the control unit is placed in the inactive position, thereby allowing at least the reservoir, the catheter and the fixation member of the irrigation device to be in fluid communication, either before or after the catheter is removed from the site of irrigation.

12. The method according to claim 10 wherein the irrigation device is used for rectal irrigation.

13. The method according to claim 10, wherein the irrigation liquid is an incompressible fluid.

14. An irrigation device comprising a reservoir for an irrigating liquid, a catheter in liquid communication with the reservoir, a fixation member, at least one pump for pumping irrigation liquid from the reservoir to the fixation member or the catheter, and a control unit arranged for in a first position transferring the irrigation liquid to the fixation member and in a second position transferring the irrigation liquid to the catheter, wherein the control unit is arranged for in a third position providing a liquid path between the fixation member and the catheter for discharging irrigation liquid from the fixation member through the catheter, and means for venting the liquid communication during the pumping action.

15. The irrigation device according to claim 14, wherein the means for venting the liquid communication is a valve and/or a vent.

16. An irrigation device comprising a reservoir for an irrigating liquid, a catheter in liquid communication with the reservoir, a fixation member, means for preventing the fixation member from bursting when liquid is transferred to the fixation member, and a control unit arranged for in a first position transferring the irrigation liquid to the fixation member and in a second position transferring the irrigation liquid to the catheter, wherein the control unit is arranged for in a third position providing a liquid path between the fixation member and the catheter for discharging irrigation liquid from the fixation member through the catheter.

17. The irrigation device according to claim 16, wherein the means for preventing the fixation member from bursting during expansion is a pressure indicator, a pressure-sensitive valve, or one or more vents.

\* \* \* \* \*